United States Patent [19]
Eastman et al.

[11] Patent Number: 4,765,317
[45] Date of Patent: Aug. 23, 1988

[54] ANTERIOR POSTERIOR HEADBLOCK

[75] Inventors: William J. Eastman, St. Louis Park; Alfred A. Iversen, Waqzata, both of Minn.

[73] Assignee: PMT Corporation, Chanhassen, Minn.

[21] Appl. No.: 2,386

[22] Filed: Jan. 12, 1987

[51] Int. Cl.4 .............................................. A61H 1/02
[52] U.S. Cl. ...................................... 128/75; 128/87 B
[58] Field of Search .................... 128/87 B, 76 R, 75, 128/89 R, 89 A, 87 R, 92 A, 92 R, 68, 69

[56] References Cited
U.S. PATENT DOCUMENTS

| | | | |
|---|---|---|---|
| 678,417 | 7/1901 | Muller | 128/89 A |
| 2,166,229 | 7/1939 | Anderson | 128/87 B |
| 2,672,146 | 3/1954 | Touson | 128/89 A |
| 2,820,455 | 1/1958 | Hall | 128/87 B |
| 3,957,040 | 5/1976 | Calabrese | 128/75 |
| 4,383,523 | 5/1983 | Schurman | 128/75 |
| 4,541,421 | 9/1985 | Iversen et al. | 128/87 B |

Primary Examiner—Edgar S. Burr
Assistant Examiner—Huong Q. Pham
Attorney, Agent, or Firm—Hugh D. Jaeger

[57] ABSTRACT

Widely adjustable anterior posterior headblock in a halo vest fixation system of graphite and other material for fixation of a head about an orthopedic jacket with respect to the cervical region, such as for spinal trauma. A slotted adjustment carrier member with ball, sockets and clamping screws at each end of the carrier fits over and between pairs of upright rods. Clamping screws and a slot in the carrier member provide for anterior and posterior movement of a saddle and an attached vertically aligned halo ring traction plate to position an attached halo ring. The halo ring traction plate moves vertically in a slot via an independent-acting, internally-captured adjustment screw to provide for vertical traction or distraction as applied to the halo ring. The halo ring rotates pivotally about a pitch axis to provide for flexion or extension adjustment of the halo ring.

4 Claims, 5 Drawing Sheets

ANTERIOR POSTERIOR HEADBLOCK

BACKGROUND OF THE INVENTION

1. Field of the Invention

The present invention pertains to a surgical appliance, and more particularly, pertains to a widely adjustable anterior-posterior headblock for use in conjunction with a halo fixation system for use as an orthotic or orthopedic brace following surgery or accidents where there is trauma to the spine.

2. Description of the Prior Art

Prior art halo ring adjustment systems allow for limited traction/distraction and flexion/extension adjustment capabilities with no allowance for anterior-posterior adjustment of the halo ring without the loss of traction.

Prior art systems use a minimum of only one clamping screw. If the clamp comes loose, adjustment and alignment might be misaligned.

Other prior art includes the "test tube rack" overhead superstructure which consists of round rods connected by clamps which are quite cumbersome, both in application and appearance, and are often made of X-ray incompatible materials such as steel, aluminum or other like materials which reduce the scanning capabilities of the X-ray system.

Prior art adjustment system also include notched style adjustments with another point of adjustment located on the orthopedic jacket some distance from the halo area on the halo jacket.

The present invention overcomes the disadvantages of the prior art by providing an anterior-posterior headblock system comprised of composite materials which offer a wide range of infinite incremental traction/distraction, anterior-posterior, and flexion/extension adjustments at the upper halo level; and more importantly, provides for full adjustment without the loss of traction during adjustment.

SUMMARY OF THE INVENTION

The general purpose of the present invention is to provide a anterior-posterior headblock assembly for use with a halo system for fixation of the cervical neck region following trauma to the spine. The components are of a light-weight material and are secured through a ball, rod and screw assembly to a halo fixation jacket to allow complete tilt-angulation and elevational, as well as longitudinal, adjustment to the halo. The halo headblock assembly provides for X-ray, CT and MRI compatibility, or the like, while the patient is wearing the system, and a low profile above the patient's head is maintained. The headblock assembly, often referred to as the anterior-posterior headblock, provides greater adjustment in the flexion/extension and traction/distraction ranges. Anterior-posterior, traction/distraction and flexion/extension adjustments of the halo ring are available without the loss of traction.

According to one embodiment of the present invention, there is provided a widely adjustable anterior-posterior headblock for a halo fixation system, including infinite incremental adjustment and overall vertical adjustment of the main body ball and socket carrier on rods inserted through screw clamped sockets. Pivotal flexion or extension adjustment of the halo ring is achieved through the use of clamping bolts positioned through radiused slots in a traction plate and secured to the halo ring. Anterior or posterior positional adjustment of the halo is allowed via a connecting sliding adjustment saddle and halo ring traction plate, which, as a unit, secures with bolts to and slides within a horizontally aligned slot in the ball and socket carrier. Fine vertical positioning of the halo is provided by an adjustable halo ring traction plate which adjusts vertically by an adjustment screw engaged within the adjustable saddle and halo ring traction plate.

One significant aspect and feature of the present invention is a anterior-posterior headblock system which provides for a halo flexion/extension adjustment by use of a radius slot in a halo ring traction plate without the loss of traction.

Another significant aspect and feature of the present invention is an anterior-posterior slotted head-block adjustment system which provides for longitudinal halo positioning without the loss of traction by use of a sliding member.

Yet another significant aspect and feature of the present invention is a traction/distraction adjustment system which provides for vertical halo positioning without the loss of traction by use of a screw actuated halo ring traction plate.

Still another significant aspect and feature of the present invention is a headblock system using graphite bars, balls and sockets for attachment of the headblock to the halo vest.

Another significant aspect and feature of the present invention is that whereby all clamping points are secured by at least two or more separate screws or devices to prevent the possibility of misalignment of a halo by a securing device or screw which has worked itself loose.

Another significant aspect and feature of the present invention is a halo fixation system which provides for computer-tomography (CT) compatibility, nuclear magnetic resonance imaging (MRI) compatibility, and X-ray compatibility, especially in the cervical area.

A further significant aspect and feature of the present invention is that the halo fixation system is light weight.

An additional significant aspect and feature of the present invention is the ease of assembly and attachment to the patient, along with security of attachment.

Having thus described the embodiments of the present invention, it is the principal object hereof to provide a halo fixation anterior-posterior headblock system.

One object of the present invention is to provide a halo fixation headblock system which provides for traction/distraction, anterior-posterior and flexion adjustment without the loss of traction.

Another object of the present invention is to provide a halo fixation headblock system which is easily utilized by medical personnel.

A further object of the present invention is a halo fixation headblock system which is low cost and disposable, providing for one time usage.

BRIEF DESCRIPTION OF THE DRAWINGS

Other objects and many of the attendant advantages of the present invention will be readily appreciated as the same becomes better understood by reference to the following detailed descriptions when considered in connection with the accompanying drawings, in which like reference numerals designate like parts throughout the figures thereof and wherein.

DESCRIPTION OF THE PREFERRED EMBODIMENTS

Figure 1:
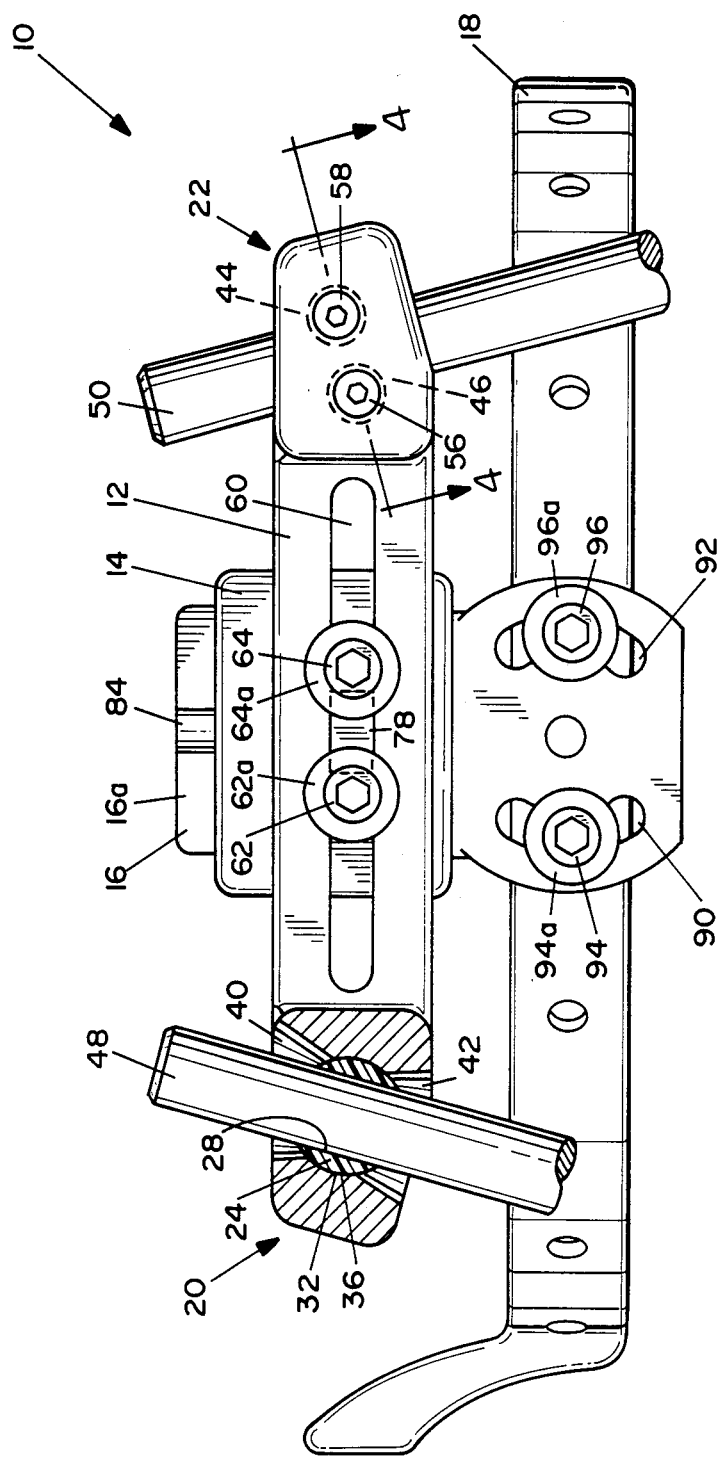
FIG. 1 illustrates a side view of the anterior-posterior headblock, the present invention, attached to a halo ring.

FIG. 1 illustrates a side view of the anterior-posterior headblock 10, the present invention, attached to a halo ring 18. The headblock 10 includes a main body ball and socket carrier 12, adjustable saddle 14 and a halo ring traction plate 16. Located at opposing ends of the main body ball and socket carrier 12 are ball and socket clamping devices 20 and 22, each similar to each other and a mirror image of each other. The ball and socket clamping devices 20 and 22, shown in cross section, include thermoplastic bushings 24 and 26, such as nylon or the like compressible material.

Figure 2:
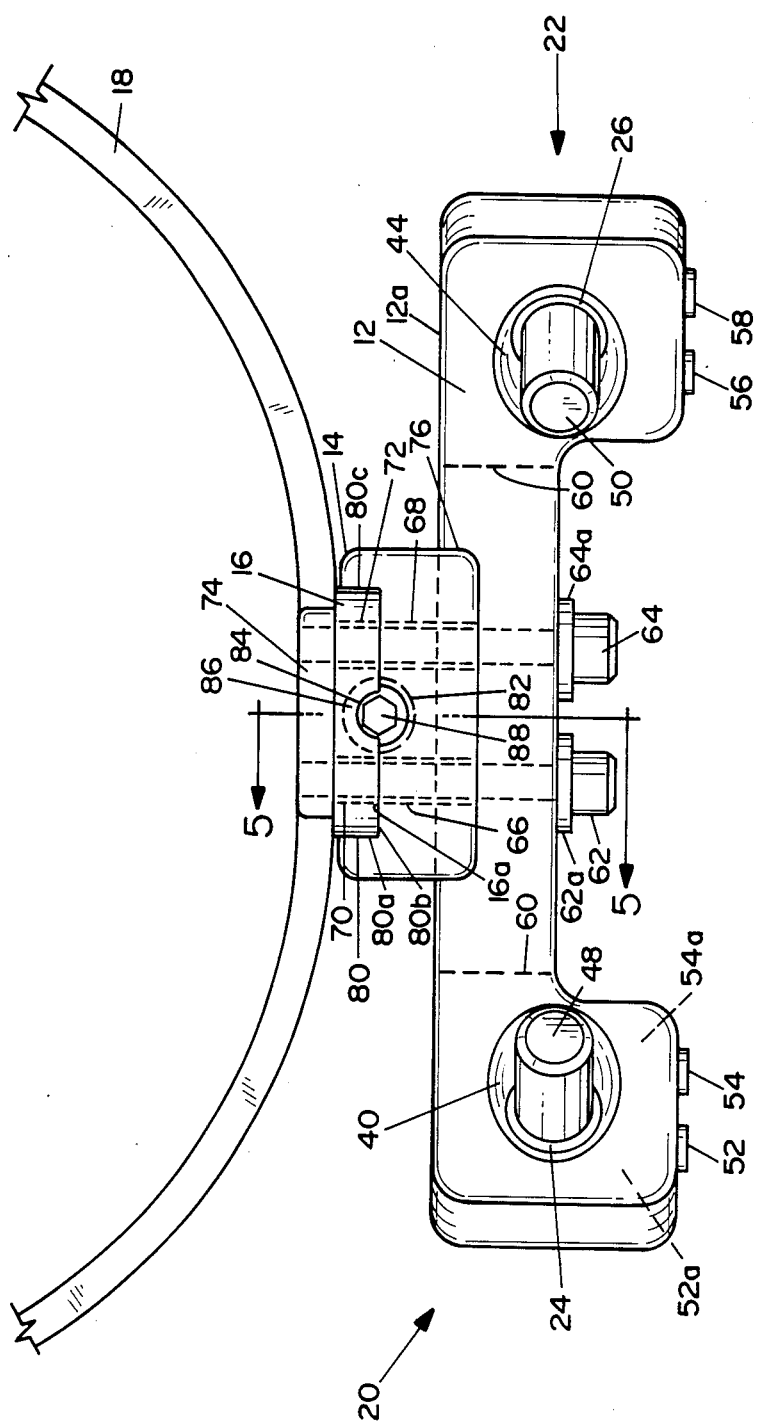
FIG. 2 illustrates a top view of the headblock with an attached halo ring.
Figure 4:
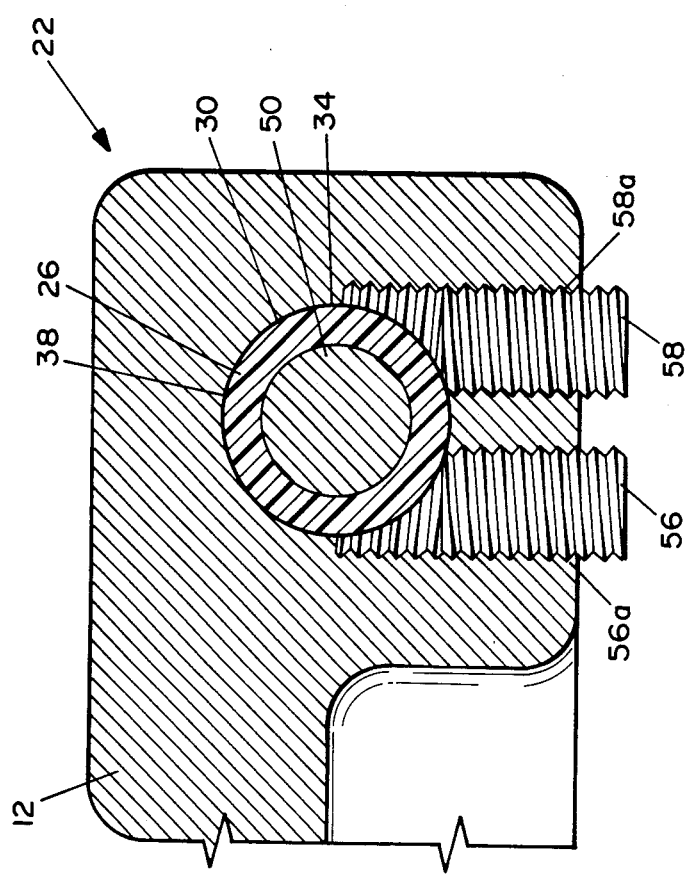
FIG. 4 illustrates a fragmental cross-sectional view of a ball and socket clamping device taken along line 4—4 of FIG. 1; and, FIG. 5 illustrates a cross-sectional view taken along line 5—5 of FIG. 2 of the traction adjustment screw between the adjustable saddle and the halo ring traction plate.

Reference is now made to FIGS. 1 and 4 where thermoplastic bushings 24 and 26 include cylindrical inner surfaces 28 and 30, respectively, and spherical outer surfaces 32 and 34, respectively, which sit within spherical seats 36 and 38, respectively. Configured conical tapered openings 40, 42, 44 and 46 allow for angular positioning of cylindrical graphite halo uprights 48 and 50 as the anterior-posterior headblock 10 is adjusted, as later described in detail. The cylindrical graphite halo uprights 48 and 50 slide within the cylindrical inner surfaces 28 and 30 in the thermoplastic bushings 24 and 26. The cylindrical graphite halo uprights 48 and 50 extend downwardly to attach to a suitable halo vest such as that described in U.S. Pat. No. 4,541,421, assigned to the assignee of this patent. Positioning and fixing of the cylindrical graphite halo uprights 48 and 50, as well as other uprights not illustrated for purposes of brevity and clarity, within the main body ball and socket carrier 12 is achieved by the tightening of ball and socket clamping pairs of screws 52 and 54, 56 and 58 in threaded holes 52a, 54a, 56a, and 58a, respectively, referred to in this FIG. and FIG. 4 after the anterior-posterior headblock 10 is aligned vertically on the cylindrical graphite halo uprights 48 and 50 and as later described in detail. A horizontally aligned anterior-posterior adjustment slot 60 positions between the ball and socket clamping devices 20 and 22 in the main body ball and socket carrier 12. Anterior-posterior slot clamping bolts 62 and 64, including washers 62a and 64a, position through the anterior-posterior adjustment slot 60, into body holes 66 and 68 in the adjustable saddle 14, through slotted body holes 70 and 72 in the halo ring traction plate 16, and into a dual threaded hole nut plate 74, securing the main body ball and socket carrier 12, the adjustable saddle 14 and the halo ring traction plate 16 together, as also illustrated in FIG. 2. The adjustable saddle 14, the halo ring traction plate 16 and the halo ring 18, along with the anterior-posterior slot clamping bolts 62 and 64, as a unit, are adjusted laterally, i.e. anteriorly or posteriorly within horizontally aligned anterior-posterior adjustment slot 60, with respect to the main body ball and socket carrier 12 to facilitate lateral adjustment.

Figure 5:
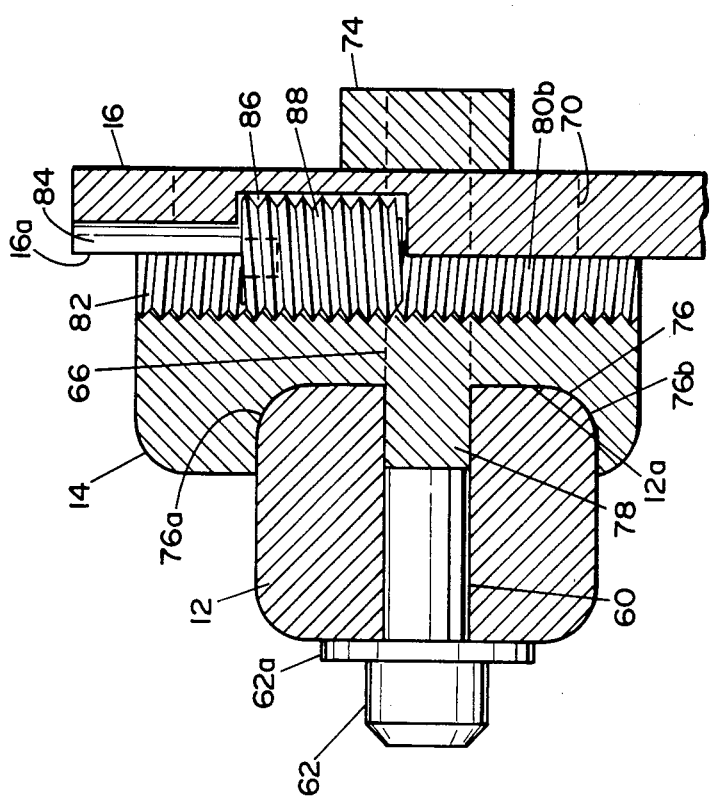

FIG. 2 illustrates a top view of the anterior-posterior headblock 10 where all numerals correspond to those elements previously described. The configured adjustable saddle 14 includes two configured channels or slots. A horizontally aligned slot or channel 76, also illustrated in FIG. 5, includes rounded inner radiused channel corners 76a and 76b which conform to the cross section of the main body ball and socket carrier 12. Slot 76 rests and slides laterally over and about surface 12a of the main body ball and socket carrier 12. A centrally located rectangular block alignment member 78, which is optional, integral to the adjustable saddle 14, slides laterally within the anterior-posterior adjustment slot 60 to further guide and align the adjustable saddle 14 for adjustment laterally along surface 12a on the main body ball and socket carrier 12. Another three-sided vertically aligned slot or channel member 80, including surfaces 80a, 80b and 80c, positions on the face opposite aligned slot 76 of the adjustable saddle member 14 in which the halo ring traction plate 16 adjusts vertically, as later described in detail. A threaded half hole 82 positions vertically and centrally on surface 80b in aligned slot member 80, as also illustrated in FIG. 5. The halo ring traction plate 16 includes a vertically aligned half body hole 84 positioned on face 16a of the halo ring traction plate 16 which aligns adjacent to threaded half hole 82. A capture cavity 86 positions below the half body hole 84 in the halo ring traction plate 16. A traction adjustment screw 88 positions partially in the threaded half hole 82 of the adjustable saddle 14, partially within the capture cavity 86 in the halo ring traction plate 16 to effect a vertical adjustment of the halo ring traction plate 16, and affixed halo ring 18 as the traction adjustment screw 88 is rotated, as also illustrated in FIG. 5. Turning the traction adjustment screw 88 moves the adjustment screw 88 up and down in the adjustable saddle 14, and since the adjustment screw 88 is captured in the halo ring traction plate 16, the halo ring traction plate 16 also moves vertically in relation to the adjustable saddle 14. In addition to slotted body holes 70 and 72, the halo ring traction plate 16 also contains radius slots 90 and 92, including halo clamp screws 94 and 96 and washers 94a and 96a for extension tilt adjustment of the halo ring 18 relative to the anterior-posterior headblock 10, as also illustrated in FIGS. 1 and 3.

Figure 3:
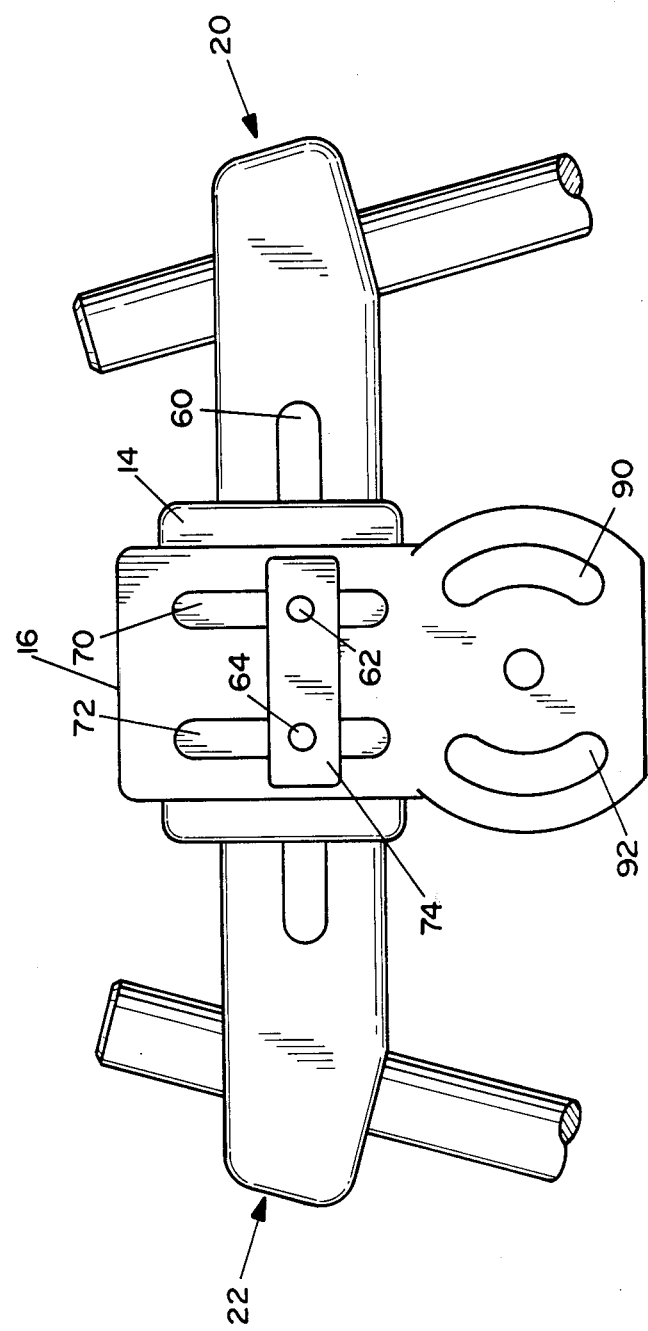
FIG. 3 illustrates a left side elevational of the headblock.

FIG. 3 illustrates a left side elevation of the anterior-posterior headblock where all numerals correspond to those elements previously described. Shown in particular are slotted body holes 70 and 72 which allow for traction or detraction vertical fine adjustment and movement of the halo ring traction plate 16, along with halo ring 18 with respect to the adjustable saddle 14 and the main body ball and socket carrier 12. Also shown is the nut plate 74 against which slot clamping screws 62 and 64 tighten after adjustment of the traction adjustment screw 88.

FIG. 4 illustrates a cross-sectional view of a ball and socket clamping device 22 taken along line 4—4 of FIG. 1 where all numerals correspond to those element previously described. Thermoplastic bushing 26 with cylindrical inner surface 30 and spherical outer surface 34 is positioned in spherical seat 38 as previously described. Halo upright 50 passes through the hole formed by the cylindrical inner surface 30 in the thermoplastic bushing 26 and extends downward to the halo vest. Fixation of the halo upright 50 within the main body ball and socket carrier 12 is achieved by tightening clamping screws 56 and 58 in threaded holes 56a and 58a against bushing 26 to deform the thermoplastic bushing 26 and secure the halo upright 50 within thermoplastic bushing 26.

FIG. 5 illustrates a cross-sectional view of the traction adjustment screw 88 engaged between the adjustable saddle 14 and the halo ring traction plate 16 taken along line 5—5 of FIG. 2, where all numerals correspond to those elements previously described. Shown in particular is the engagement of the traction adjustment screw 88 in the threaded half hole 82 of the adjustable saddle 14, and also in the capture cavity 86 of the halo ring traction plate 16. As previously described, slot clamping bolts 62 and 64 pass through the anterior-posterior horizontally adjustment slot 60, body holes 66 and 68, through slotted body holes 70 and 72 and into the dual threaded hole nut plate 74. The optional alignment member 78 is also illustrated projecting into anterior-posterior adjustment slot 60. To effect anterior and posterior movement of adjustable saddle 14 laterally along and about the anterior-posterior horizontal adjustment slot 60, slot clamping bolts 62 and 64 are loosened slightly to allow anterior-posterior adjustment of the saddle 14. Vertical movement of the adjustable saddle 14, the halo ring traction plate 16, and the halo ring 18, with respect to the main body ball and socket carrier 12, is unaffected because traction adjustment screw 88 is engaged within threaded half holes 82 and capture cavity 86 to provide for positive vertical positioning between the adjustable saddle 14 and the halo ring traction plate 16.

MODE OF OPERATION

A halo ring 18 and halo vest positions on a patient according to standard conventional and known techniques. Only one anterior-posterior headblock assembly 10 is illustrated, although two are used to support the halo ring 18. The headblock assembly 10 is attached to the halo 18 using halo ring clamp screws 94 and 96. With halo clamp bolts 94 and 96 loosened slightly, the headblock assembly 10 is adjusted such that the main body ball and socket carrier 12 is substantially parallel to the ground when the patient is in an upright position. The halo clamp bolts 94 and 96 are then tightened with a wrench, in this case an Allen head wrench, which is the same size required for adjustments to other screws in the headblock 10 assembly. Ball and socket clamping devices 20 and 22 position over halo uprights 48 and 50 which in turn attach to a halo vest and are secured with ball and socket clamping bolts pairs 52 and 54, and 56 and 58. The patient's bodily position is then verified via various scanning techniques and if a flexion or extension adjustment is deemed necessary, halo clamp bolts pairs 94 and 96 can be loosened slightly and rotation of the halo ring 18 is then made until proper flexion or extension is achieved, at which point halo clamp bolts 94 and 96 are retightened.

Final traction and distraction adjustments are made by slightly loosening the slot clamping screw pair 62 and 64, turning the traction adjustment screw 88 counterclockwise for traction and clockwise for distraction, and then retightening slot clamping bolts 62 and 64. Anterior and posterior lateral adjustment is accomplished by loosening slot clamping bolts 62 and 64 and sliding the adjustable saddle 14, along with the attached halo ring traction plate 16 and halo ring 18 horizontally, i.e. anteriorally or posteriorally along the main body ball and socket carrier 12, and then retightening slot clamping screws 62 and 64 when the desired lateral adjustment is achieved. Each adjustment can be made infinitely small and over an appropriate range of adjustability, and can be made without degradation of other adjustments. Anterior-posterior adjustment, as well as traction/distraction and flexion/extension adjustments, can be made without the loss of traction due to the configuration of the traction adjustment screw, which is essentially unaffected by the minor loosening of the slot clamping bolts 62 and 64.

Various modifications can be made to the present invention without departing from the scope thereof.

What we claim is:

1. In a halo fixation device attached to an orthopedic jacket by two pairs of rods, an improved headblock assembly comprising:
    a. main body carriers, each slidably and pivotally mounted for horizontal, vertical and lateral movement relative to each pair of said rods, and ball and socket clamping devices for securing said main body carriers in place on said rods, said main body carriers each having a substantially horizontal aligned adjustment slot;
    b. adjustable saddles, each slidably mounted for horizontal movement on one of said main body carriers, and means for securing each of said adjustable saddles in place on each of said main body carriers; and, halo ring traction plates, each having vertical opposing slotted body holes and opposing radiused slots;
    c. a halo ring secured to said halo traction plates, and means for securing said halo ring in place on said halo ring traction plate.

2. The device of claim 1 wherein said means for securing each of said adjustable saddles in place on each of said main body carriers are bolts.

3. The device of claim 1 wherein said means for securing said halo ring in place on said halo ring traction plates are bolts.

4. The device of claim 1 having four rods, and two main body carriers and two adjustable saddles.

* * * * *